US00PP29847P2

(12) United States Plant Patent
Hemstad et al.

(10) Patent No.: US PP29,847 P2
(45) Date of Patent: Nov. 20, 2018

(54) GRAPEVINE PLANT NAMED 'ITASCA'

(50) Latin Name: ***Vitis* spp. hybrid**
Varietal Denomination: Itasca

(71) Applicant: Regents of the University of Minnesota, Minneapolis, MN (US)

(72) Inventors: Peter Hemstad, Edina, MN (US); Nicholas Smith, Sauk City, WI (US); Kathryn Cook, Montour Falls, NY (US); John Thull, Excelsior, MN (US); James Luby, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/530,394

(22) Filed: Jan. 9, 2017

Related U.S. Application Data

(60) Provisional application No. 62/387,956, filed on Jan. 11, 2016.

(51) Int. Cl.
*A01H 5/08* (2018.01)

(52) U.S. Cl.
USPC ..... Plt./207

(58) Field of Classification Search
USPC ..... Plt./207, 205
CPC ..... A01H 5/0812; A01H 5/08; A01H 6/88
See application file for complete search history.

(56) References Cited

PUBLICATIONS

Ganchiff et al North Dakota State University Plant Science Vineyard & Winery Management Magazine Mar./Apr. 2015, retrieved on Feb. 9, 2018, retrieved from the Internet at https://www.ag.ndsu.edu/plantsciences/news/ graduate-research-on-grapes-featured-in-wine-trade-magazine, pp. 1-7. (Year: 2015).*

Regents of the University of Minnesota Itasca Joins List of Released Cold-Hardy Wine Grapes 2016, retrieved on Feb. 12, 2018, retrieved from the Internet at https://mnhardy.umn.edu/itasca-grape, pp. 1-3. (Year: 2016).*

* cited by examiner

*Primary Examiner* — June Hwu
(74) *Attorney, Agent, or Firm* — Penny J. Aguirre

(57) ABSTRACT

The invention is a new and distinct variety of grapevine plant named 'Itasca', which is characterized by its adaptibility to grow in cold climates for grape production, its cold hardiness to at least U.S.D.A. Zone 4, its fruits that are suitable for making white wine, its fruit with moderately low total acidity levels combined with high sugar levels at maturity, and its high resistance to downy mildew and black rot diseases and moderate resistance to powdery mildew and foliar infestation by the insect pest phylloxera.

2 Drawing Sheets

STATEMENT REGARDING FEDERALLY SPONSORED RESEARCH

This invention was made with government support under 2008-34360-19469 and 2010-34360-21351 awarded by the National Institute of Food and Agriculture, USDA. The government has certain rights in the invention.

Botanical classification: *Vitis* spp. hybrid.

Variety denomination: 'Itasca'.

BACKGROUND OF THE INVENTION

The present invention relates to a new and distinct cultivar of grape plant botanically known as *Vitis* spp. hybrid 'Itasca', referred to hereafter by its cultivar name, 'Itasca'.

'Itasca' originated from a cross made in 2002 between the *Vitis* spp. hybrid cultivar 'Frontenac gris' (U.S. Plant Pat. No. 16,478) as the female parent and an unpatented *Vitis* spp. hybrid plant from the Inventors' breeding program, designated as 'MN1234' as the male parent.

Asexual propagation of the new cultivar was first accomplished by hardwood stem cuttings in 2009 by the Inventors at a research center near Excelsior, Minn. Asexual propagation of the new cultivar by hardwood stem cuttings has determined that the characteristics are stable and true to type in successive generations.

SUMMARY OF THE INVENTION

The following traits have been repeatedly observed and represent the characteristics of the new cultivar. These attributes in combination distinguish 'Itasca' as a new and unique cultivar of *Vitis*.

1. 'Itasca' is well adapted to grow in viticultural regions with relatively cool summer climates and cold winter climates.
2. 'Itasca' has been shown to be cold hardy to at least U.S.D.A. Zone 4.
3. 'Itasca' produces fruits that are suitable for making white wine.
4. 'Itasca' exhibits fruit with moderately low total acidity levels combined with high sugar levels at maturity.
5. 'Itasca' has shown high resistance to downy mildew and black rot diseases and moderate resistance to powdery mildew and foliar infestation by the insect pest phylloxera.
6. 'Itasca' exhibits fig-like shaped leaves.

'Frontenac gris', the female parent plant of 'Itasca', is similar to 'Itasca' in cold hardiness, resistance to downy mildew and powdery mildew, fruit harvest date and sugar level. 'Frontenac gris' differs from 'Itasca' in having a higher susceptibility to foliar phylloxera pest, and in having fruit with substantially higher total acidity levels.

'MN1234', the male parent of 'Itasca' differs from 'Itasca' in that, at harvest, 'MN1234' has dark blue fruit and 'Itasca' has greenish yellow fruit.

'Itasca' can also be compared to the *Vitis* cultivar 'Frontenac blanc' (not patented), which is similar to 'Itasca' in cold hardiness, resistance to downy and powdery mildew and fruit harvest date and sugar level but differs from 'Itasca' in having a higher susceptibility to foliar phylloxera infestation, and in having fruit with substantially higher total acidity levels.

BRIEF DESCRIPTION OF THE DRAWINGS

The accompanying color photographs represent typical mature berry clusters and vines of 'Itasca' as grown under standard field conditions in Excelsior, Minn. The photographs were taken in September of a grapevine 10 years in age.

The photograph in FIG. 1 provides a view of a vine in fruit of 'Itasca'.

Figure 1:
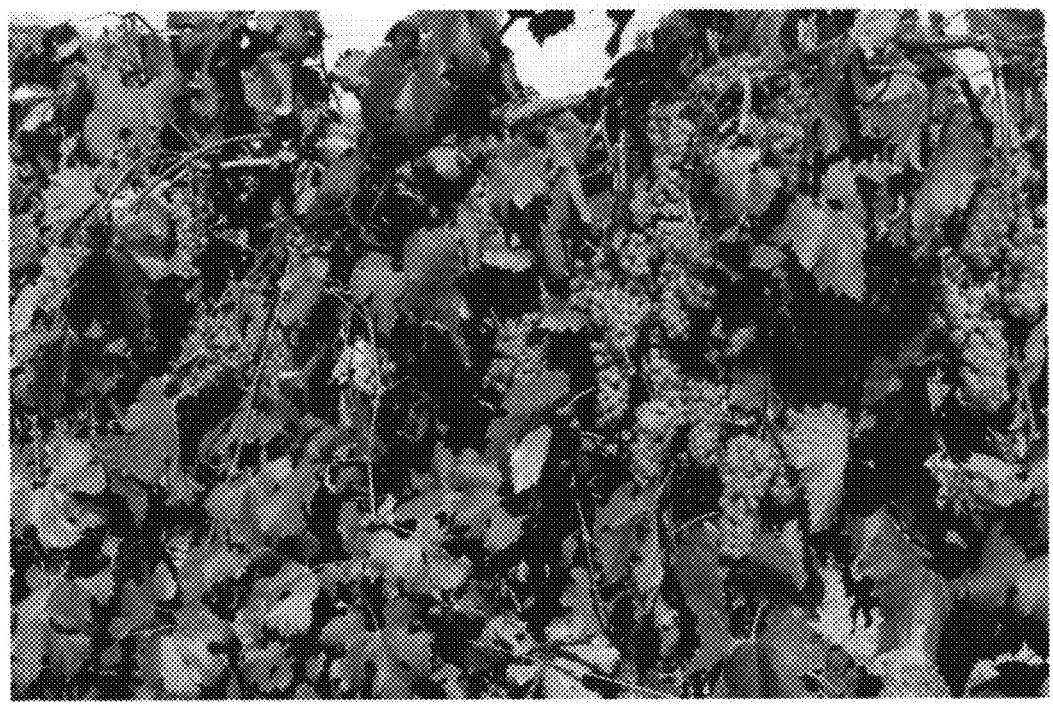
Figure 2:
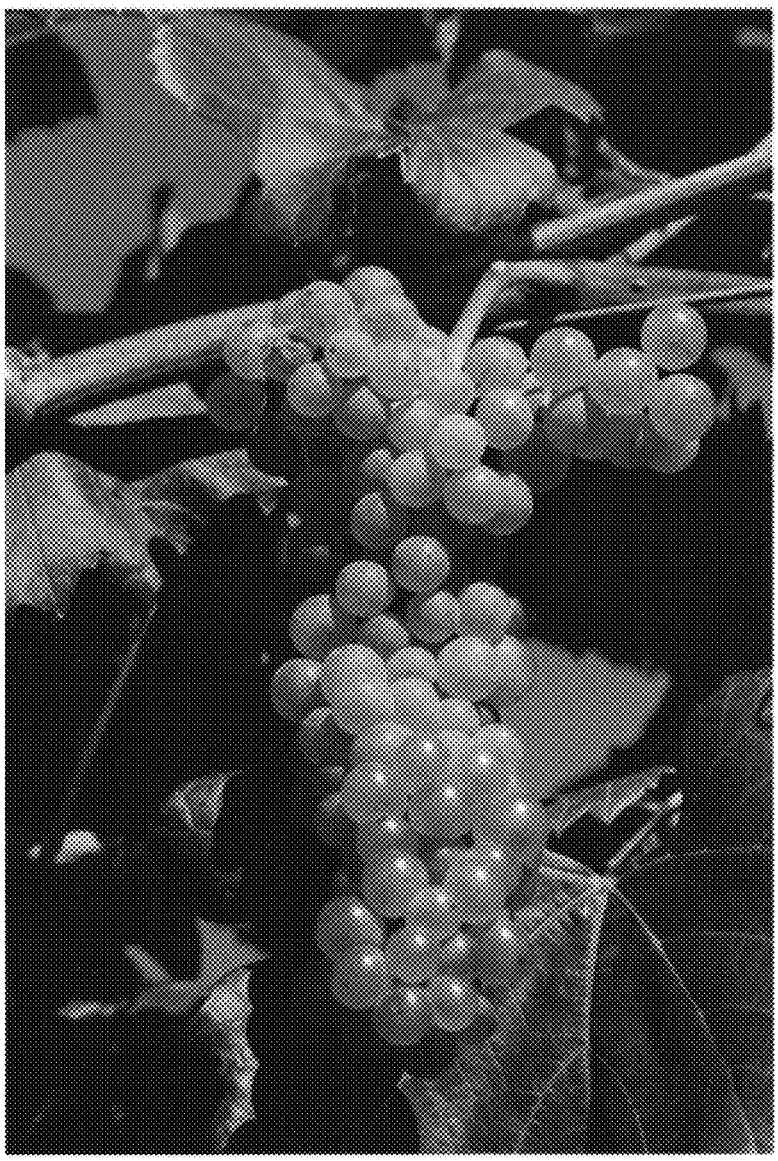

The photograph in FIG. 2 provides a close-up view of a typical fruit cluster of 'Itasca'.

The colors in the photographs are as close as possible with the photographic and printing technology utilized and the values cited in the detailed botanical description accurately describe the colors of the new grapevine.

DETAILED BOTANICAL DESCRIPTION

The following traits have been repeatedly observed and represent the characteristics of the new cultivar. The measurements, observations and descriptions that follow describe a plant 12 years in age as grown outdoors in a trial vineyard in Excelsior, Minn. with detailed botanical data collected during the 2015 growing season. 'Itasca' has not been observed under all possible environmental conditions and the phenotype may vary somewhat with variations in temperature, day length, light intensity, soil types and water and fertility levels, pruning, pest control and other cultural practices without, however, any variance in the genotype.

Many of the descriptors are based on those set forth by the International Board for Plant Genetic Resources in collaboration with the Office Internationale de la Vigne et du Vin (OIV) and the International Union for the Protection of New Varieties of Plants. All dimensions are given as means. The color determination is in accordance with The 2015 R.H.S. Colour Chart of The Royal Horticultural Society, London, England, except where general color terms of ordinary dictionary significance are used.

General characteristics:

Mature canes:

*Color of canes.*—A blend of 175A and 175C.
*Length of canes.*—1.65 m.
*Diameter of canes.*—8 mm.
*Internode length.*—11 cm.
*Lenticels.*—1 mm in length and width, round in shape, 200A in color, 16 per area 5 mm in width and 1 cm in length.
*Cane cross-section shape.*—Oval to round.
*Density of hairs on mature cane.*—None.
*Tendril pattern on shoot.*—2,0,2,0 etc. (two nodes with a tendril followed by one node without).
*Tendrils forked.*—Yes.
*Tendril texture.*—Glabrous.
*Tendril length.*—6.6 to 15 cm in length, 2 mm in width.
*Tendril color.*—Color on young shoots 146C with striations of 59C, mature 166C.
*Bud width.*—4 mm.
*Bud length.*—6 mm.
*Bud shape.*—Triangular.
*Bud color.*—A blend of 165A and 166A.
*Bud burst.*—Medium.

Trunk:

*Bark texture.*—Somewhat flaky, small vertical segments approximately 5 mm in with and 5 cm in length.
*Bark color.*—Striated, N200A, N200B, and 166A.

Mature leaves: Descriptors including the designations N1 through N5, relate to "OIV-Code Numbers 065-093" of *Preliminary Minimal Descriptor List for Grapevine Varieties* (Dettweiler E., 1991, Institüt fur Rebenzüchtung, Geilweilerhof, Germany).

*Length of blade.*—14.2 cm.
*Width of blade.*—13.9 cm.
*Shape of blade.*—Fig-like.
*Number of lobes.*—5.
*Blade margins.*—Incised into lobes with lobes deeply serrated.
*Length of primary (midrib) vein N1 from the tip of the blade to the petiole sinus.*—12.5 cm.
*Length of vein N2 from the tip of the first major lobe of the blade to the petiole sinus.*—12 cm.
*Length of vein N3 from the tip of the second major lobe of the blade to the petiole sinus.*—9.5 cm.
*Length of vein N4 from the tip of the third major lobe of the blade to where it joins the vein measured in N3.*—5.5 cm.
*Length of vein N5 from the tip of the first tooth proximal to the petiole sinus to where it joins the vein measured in N4.*—3 cm.
*Length of N2 teeth.*—1.8 cm.
*Width of N2 teeth.*—1.3 cm.
*Length/width ratio of N2 teeth.*—1.38 cm.
*Length of N4 teeth.*—1.2 cm.
*Width of N4 teeth.*—1.2 cm.
*Length/width ratio of N4 teeth.*—1 cm.
*Shape of teeth.*—Convex.
*Shape of petiolar sinus.*—Wide open.
*Shape of base of petiolar sinus.*—Lyre-shaped.
*Depth of petiolar sinus.*—3.7 cm.
*Width of petiolar sinus.*—4.2 cm.
*Petiole.*—9 cm in length, 3 mm in width, 144A to 144B in color and suffused with 183B on sun exposed side.
*Shape of upper sinuses.*—Urn-shaped.
*Shape of base of upper sinuses.*—None.
*Pubescence on adaxial surface.*—None.
*Pubescence on abaxial surface.*—Very small erect hairs on veins.
*Color of adaxial leaf surface.*—Color between NN137A and 137A, veins 145B.
*Color of abaxial leaf surface.*—138A, veins 195C.
*Color of leaf petiole.*—N144A suffused with 183A.
*Center lobe size.*—8.5 cm in length and 7.5 cm in width.

*Lateral lobe size.*—5.5 cm in length and width.
*Basal lobe size.*—6.54 cm in length and 5.57 cm in width.

Young shoots:
*Form of shoot tip.*—Mainly open.
*Density of prostate hairs on tip.*—Moderately pubescent.
*Density of erect hairs on tip.*—None observed.
*Petiole pigmentation.*—A blend of 144A and 144B and striated and suffused with 183B on sun exposed side.
*Shoot attitude.*—Semi-erect.
*Shoot pigmentation (internodes and nodes).*—A blend of 144A and 144B and striated and suffused with 183B on the dorsal side and a blend of 144A and 144B with very slight hints of 183B on the ventral side.
*Young leaves.*—137B in color on upper surface, a blend of 138A and 138B on lower surface, surface slightly satiny on upper surface and satiny on lower surface, veins upper surface 144C in color surface, lower surface 146C in color and densely pubescent on main veins only.

Flowers:
*Fragrance.*—Moderately fragrant.
*Mean time of flowering.*—June 15 when grown in Excelsior, Minn.
*Color of calyx.*—143C.
*Sepal number.*—5, sepals fused into continuous calyx.
*Calyx shape.*—Ring-shaped.
*Calyx size.*—<1 mm in length, 2 mm in width.
*Calyx apex.*—Fused to ovary.
*Calyx base.*—Fused to pedicel.
*Nectary.*—1.5 mm in diameter, <1 mm in length, N144A in color.
*Calyx surface.*—Glabrous.
*Petals.*—5, fused in calyptra cohering at summit; 2.5 mm in width and 1 mm in depth and separating at base; 4 mm in width, 2 mm in depth; reflexed after dehiscence, 144A in color.
*Shape of cluster.*—Slightly conical, reduced shoulders.
*Size of cluster.*—8 cm in length, 4.2 mm at base (2 mm at mid section).
*Number of flowers.*—Average of 167 and up to 70 on wings if present.
*Flower buds.*—4 mm in length, 2.5 mm in width, a blend of 144A and 144B in color, oblanceolate in shape, glabrous surface.
*Size of individual entire flower.*—4 mm in height, 1.1 cm in width (to end of stamens).
*Pollen fertility.*—Fertile based on use in controlled crosses.
*Reproductive organs.*—Fully developed stamens and fully developed gynoecium.
*Color of stamen.*—Anther: 21D, Filament: 160B.
*Stamen number.*—Average of 5.0.
*Filament length.*—6 mm.
*Anther.*—1.5 mm in length.
*Pollen quantity and color.*—Abundant and 15B in color.
*Pistil.*—1, ovary is 1.5 mm in length and 1 mm in width at base, urn-shaped, glabrous surface color 144B, stigma 1 mm in width and <1 mm in length, color a blend between 20B and 144B.
*Pedicel.*—3.5 mm and <1 mm in width, surface glabrous, color 143C.
*Peduncle.*—To base of cluster 4.5 cm and 2 mm in with, glossy surface and 144A suffused with 183B.

Fruit:
*Cluster length.*—14.8 cm.
*Cluster diameter.*—6.9 cm
*Cluster weight.*—145 g.
*Cluster density.*—Medium, average of 86 berries per cluster.
*Berry weight.*—1.27 g.
*Berry length.*—1.25 cm.
*Berry diameter at equator.*—1.25 cm.
*Berry shape.*—Round.
*Berry cross-section.*—Circular.
*Berry, color of skin.*—A blend of 147B and 147C and suffused with 175A.
*Berry, color of flesh.*—160C with weak anthocyanin presence.
*Berry firmness.*—Very firm.
*Berry, particular flavor.*—Neutral, not strongly aromatic.
*Length of pedicel.*—4 mm.
*Pedicel diameter.*—1.4 mm.
*Pedicel color.*—146B.
*Berry, separation from pedicel.*—Difficult.
*Berry, presence of seeds.*—Fully developed.
*Seed number/berry.*—2.5.
*Seed length.*—0.5 mm.
*Seed width.*—0.4 mm.
*Seed length/width ratio.*—1.25.
*Seed weight.*—0.036 g.
*Seed color.*—A blend of N199B and N199C.

Fruit: Values represent the means (with ranges in parentheses) for fruit harvested over five growing seasons 2011-2015.
*Harvest date.*—September 18 (September 12-September 26).
*Brix.*—26.06 (24.7-28.2).
*Ph.*—3.174 (3.04-3.33).
*Titratable acidity.*—10.706 (8.84-13.12) g/liter.

Vineyard performance: Based on observations compiled over five years (2011-2015).
*Susceptibility to powdery mildew (Uncinula necator).*—Low.
*Susceptibility to downy mildew (Plasmopara viticola).*—None.
*Susceptibility to black rot (Guignardia bidwellii).*—None.
*Susceptibility to grey mold (Botrytis cinerea).*—None.
*Susceptibility to foliar phylloxera (Daktulosphaira vitifoliae).*—Low.
*Susceptibility to crown gall (Agrobacterium tumefaciens).*—None.
*Susceptibility to phenoxy herbicide drift (e.g., 2,4-D).*—None.
*Berry splitting.*—None.
*Berry shelling.*—None.
*Vigor level.*—High.
*Winter hardiness.*—Moderate-high.
*Wood ripening.*—Good.

Wine quality:
*Flavors and aromas.*—Muscat, apricot, peach.
*Balance.*—Viscous.
*Color.*—Light green to gold.
*Propensity for oxidation.*—Low.
*Overall quality.*—Very good.

It is claimed:

1. A new and distinct variety of grapevine plant designated 'Itasca' as described and illustrated herein.

* * * * *